(12) United States Patent
Chiang et al.

(10) Patent No.: US 10,121,673 B2
(45) Date of Patent: Nov. 6, 2018

(54) MINIATURIZE PARTICULATE MATTER DETECTOR AND MANUFACTURING METHOD OF A FILTER

(71) Applicant: Industrial Technology Research Institute, Hsinchu (TW)

(72) Inventors: Chia-Wen Chiang, Taichung (TW); Cheng-Ta Ko, Taipei (TW); I-Hsing Lin, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 147 days.

(21) Appl. No.: 14/953,424

(22) Filed: Nov. 30, 2015

(65) Prior Publication Data

US 2017/0052102 A1 Feb. 23, 2017

(30) Foreign Application Priority Data

Aug. 19, 2015 (TW) .............................. 104127014 A

(51) Int. Cl.
| | |
|---|---|
| H01L 21/306 | (2006.01) |
| G01N 29/02 | (2006.01) |
| G01N 29/036 | (2006.01) |
| G01N 15/00 | (2006.01) |
| G01N 15/06 | (2006.01) |

(52) U.S. Cl.
CPC ..... *H01L 21/30604* (2013.01); *G01N 29/022* (2013.01); *G01N 29/036* (2013.01); *G01N 15/0606* (2013.01); *G01N 2015/0046* (2013.01); *G01N 2291/014* (2013.01); *G01N 2291/02809* (2013.01)

(58) Field of Classification Search
CPC .................. G01N 15/0656; G01N 2015/0046
USPC .............................................. 73/28.01–28.06
See application file for complete search history.

(56) References Cited

U.S. PATENT DOCUMENTS

| | | | | |
|---|---|---|---|---|
| 5,060,508 A | * | 10/1991 | Wong ................... | G01N 1/2258 |
| | | | | 356/437 |
| 5,932,795 A | | 8/1999 | Koutrakis et al. | |
| 6,750,449 B2 | | 6/2004 | Marcus | |
| 6,964,190 B2 | | 11/2005 | Shinohara et al. | |

(Continued)

FOREIGN PATENT DOCUMENTS

| | | |
|---|---|---|
| CN | 1075549 | 8/1993 |
| CN | 100464060 | 2/2009 |

(Continued)

OTHER PUBLICATIONS

Mehdizadeh et al., "A two-stage aerosol impactor with embedded MEMS resonant mass balances for particulate size segregation and mass concentration monitoring," IEEE Sensors, Nov. 3-6, 2013, pp. 1-4.

(Continued)

*Primary Examiner* — Lisa Caputo
*Assistant Examiner* — Irving A Campbell
(74) *Attorney, Agent, or Firm* — JCIPRNET

(57) ABSTRACT

In an embodiment, a miniaturize particulate matter detector includes a filter having a plurality of holes, and a concentration detector correspondingly disposed under the filter. The concentration detector has a detect area used for detecting a concentration of at least one miniaturize particulate matter. A manufacturing method of the filter is also provided.

10 Claims, 12 Drawing Sheets

(56) References Cited

U.S. PATENT DOCUMENTS

| | | |
|---|---|---|
| 7,100,423 B2 | 9/2006 | Trenholm |
| 7,168,292 B2 | 1/2007 | Gundel et al. |
| 7,254,212 B2 | 8/2007 | Saitoh et al. |
| 7,325,465 B2 | 2/2008 | Solomon et al. |
| 7,377,187 B2 | 5/2008 | Lai et al. |
| 8,225,684 B2 | 7/2012 | Kondo et al. |
| 8,534,116 B2 | 9/2013 | Wang et al. |
| 2005/0188746 A1 | 9/2005 | Shinohara et al. |
| 2008/0105034 A1* | 5/2008 | Parfitt .................. G01N 1/2208 73/28.06 |
| 2009/0314066 A1 | 12/2009 | Nieuwenhuis et al. |
| 2012/0208283 A1* | 8/2012 | Gheorghiu ......... G01N 21/1717 436/94 |
| 2012/0244037 A1* | 9/2012 | Matsumoto ............. C07F 5/025 422/69 |
| 2013/0213115 A1 | 8/2013 | Chu et al. |
| 2014/0083167 A1 | 3/2014 | Liu et al. |

FOREIGN PATENT DOCUMENTS

| | | |
|---|---|---|
| CN | 201637649 | 11/2010 |
| CN | 102590088 | 7/2012 |
| TW | 363178 | 7/1999 |
| TW | 200528179 | 9/2005 |
| TW | 200730814 | 8/2007 |
| TW | 201027060 | 7/2010 |

OTHER PUBLICATIONS

Hajjam et al., "Thermally actuated MEMS resonant sensors for mass measurement of micro/nanoscale aerosol particles," IEEE Sensors, Oct. 25-28, 2009, pp. 707-710.

Budde et al., "Enabling Low-Cost Particulate Matter Measurement for Participatory Sensing Scenarios," Proceedings of the 12th International Conference on Mobile and Ubiquitous Multimedia, Dec. 2, 2013, pp. 1-10, article No. 19.

Budde et al., "Investigating the use of commodity dust sensors for the embedded measurement of particulate matter," 9th International Conference on Networked Sensing Systems (INSS), Jun. 11-14, 2012, pp. 1-4.

Yuen et al., "Microfluidic-based real-time detector for fine particulate matter," IEEE Sensors, Nov. 2-5, 2014, pp. 775-778.

* cited by examiner of a miniaturize particulate matter detector and manufacturing method of a filter set forth herein; rather, these exemplary embodiments are provided so that this disclosure will be thorough and complete.

MINIATURIZE PARTICULATE MATTER DETECTOR AND MANUFACTURING METHOD OF A FILTER

CROSS-REFERENCE TO RELATED APPLICATION

This application claims the priority benefit of Taiwan application serial no. 104127014, filed on Aug. 19, 2015. The entirety of the above-mentioned patent application is hereby incorporated by reference herein.

TECHNICAL FIELD

The technical field relates to a miniaturize particulate matter detector and a manufacturing method of a filter.

BACKGROUND

According to World Health Organization's prediction, death rate of lung cancer may be ranking up to fifth class in the world. Currently, lung cancer is detected by the X-ray machine. However, it is discovered usually in the lung cancer last stage. Except smoking, the reasons causing the lung cancer further include particulate matters of air pollution.

Traditional monitors for detecting particulate matter concentration have a huge volume, for example, the weighing measurement machine is continuously collecting the particulate matters in the air for 24 hours, and placing the collected particulate matters on the filter paper for measuring the weight of the particulate matters, and then converting the measured weight value into the concentration value.

Cyclone-type miniaturize particulate matter filter is used to fix the air speed and select an exact size of miniaturize particulate matter. The filter has problems of huge volume and regularly cleaning to maintain the fixed air speed. Impactor-type miniaturize particulate matter filter collects the miniaturize particulate matters from the air that passes through a numbers of large, medium, small sizes of holes and a blocking plate under the holes. Cyclone-design miniaturize particulate matter filter also uses the cyclone-type scheme to collect miniaturize particulate matters. Other schemes of collecting miniaturize particulate matters include C14 measurement, optical measurement, Tape Element Oscillator Measurement (TEOM), and so on. Their principles are selecting exact miniaturize particulate matters and proceeding a mass measurement.

SUMMARY

An embodiment of the disclosure relates to a miniaturize particulate matter detector. The miniaturize particulate matter detector comprises a filter having a plurality of holes, and a concentration detector correspondingly disposed under the filter. The concentration detector has a detect area used for detecting a concentration of at least one miniaturize particulate matter.

Another embodiment of the disclosure relates to a manufacturing method of a filter. The manufacturing method comprises: providing a substrate; coating or lithographic printing a photoresist material on the substrate; etching a plurality of openings on the substrate, wherein the plurality of openings have an opening shape of gradually reducing, or gradually expanding or cylindrical; removing the photoresist material from the substrate; pasting a support plate on a surface of the plurality of openings on the substrate; grinding the substrate until to expose the plurality of openings to form a plurality of through-silicon vias (TSVs); and cutting off the substrate and including the plurality of TSVs.

The foregoing will become better understood from a careful reading of a detailed description provided herein below with appropriate reference to the accompanying drawings.

DETAILED DESCRIPTION OF DISCLOSED EMBODIMENTS

Figure 1A:
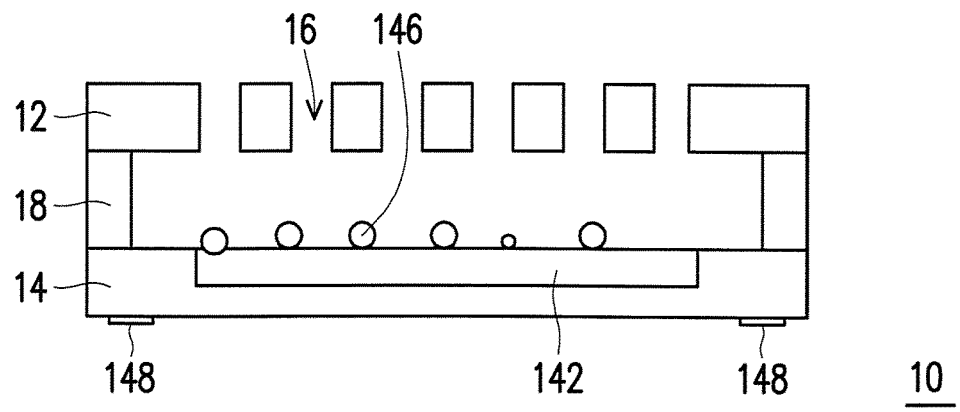
FIG. 1A is a cross-sectional schematic view of a miniaturize particulate matter detector according to a first exemplary embodiment.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

FIG. 1A is a cross-sectional schematic view of a miniaturize particulate matter detector according to a first exemplary embodiment. With reference to FIG. 1A, the miniaturize particulate matter detector 10 comprises a filter 12 and a concentration detector 14. The filter 12 has a plurality of holes 16, and the concentration detector 14 correspondingly disposed under the filter 12. The concentration detector 14 has a detect area 142 used to detect a concentration of at least one miniaturize particulate matter. In an embodiment, the opening shape of the holes 16 may be a cylindrical. The holes may be TSVs (Through Silicon Vias). In an embodiment, an adhesive material 18 may be disposed between the concentration detector 14 and the filter 12 to seal or bonding the concentration detector 14 and the filter 12 at two closer edges of the concentration detector 14 and the filter 12.

Figure 1B:
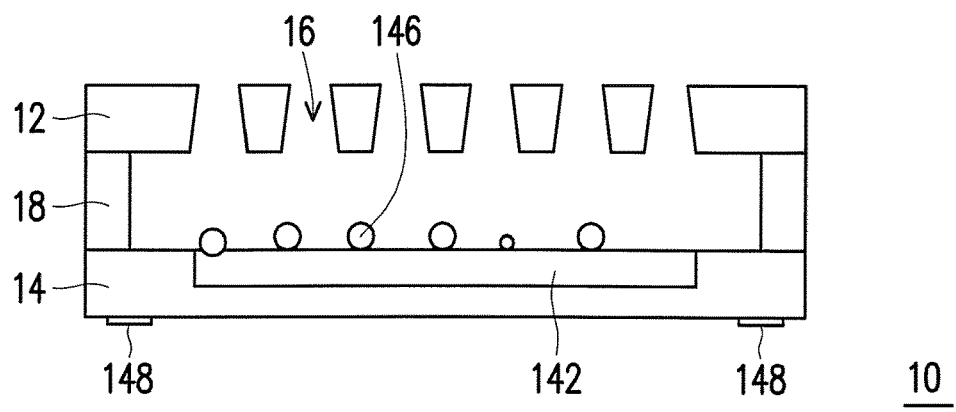
FIG. 1B is a cross-sectional schematic view of a miniaturize particulate matter detector according to a second exemplary embodiment.

FIG. 1B is a cross-sectional schematic view of a miniaturize particulate matter detector according to a second exemplary embodiment. Please refer to FIG. 1B, the structure of the miniaturize particulate matter detector in FIG. 1B is same as that in the first embodiment of FIG. 1A. The difference is the opening shape of all or part of holes 16 may be a gradually reducing shape or a gradually expanding shape. The holes 16 may be, but not limited to TSVs. Herein, the gradually reducing shape of one hole 16 is defined as a cross-sectional area of a first end (entrance end) of the hole 16 is larger than that of a second end (exit end) of the hole 16. Namely, the area of an inlet (second end) of the hole 16 is smaller than that of an outlet (first end) of the hole 16. The gradually expanding shape is defined as a cross-sectional area of a first end of the hole 16 is larger than that of a second end of the hole 16. Namely, the area of an inlet (first end) is smaller than that of an outlet (second end). In one embodiment, all or part of the plurality of holes 16 of the filter 12 may have an opening shape of the gradually reducing shape or the gradually expanding shape. The gradually reducing shape or the gradually expanding shape of the holes 16 may be regular or irregular, or the opening shape of the plurality of holes may be fixed and is the cylindrical.

Figure 1C:
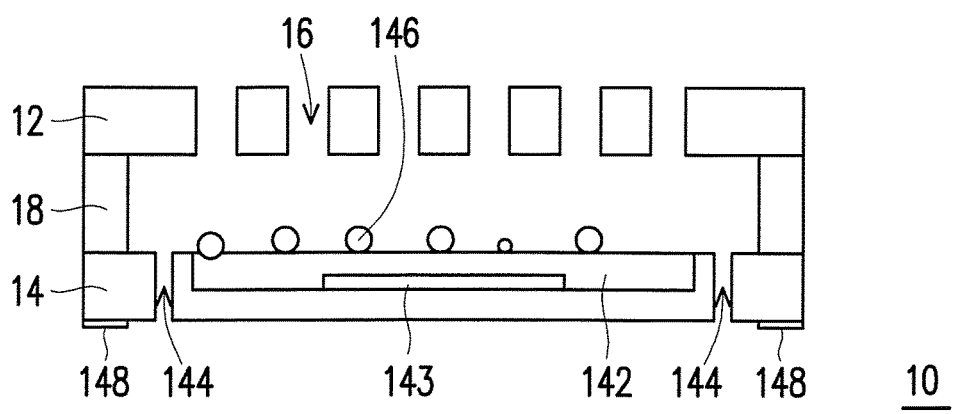
FIG. 1C is a cross-sectional schematic view of a miniaturize particulate matter detector according to a third exemplary embodiment.

Please refer to FIG. 1C, the structure of the miniaturize particulate matter detector in FIG. 1B is same as that in the first embodiment mentioned. The difference is each of two sides of the detect area 142 of the concentration detector 14 in FIG. 1C disposed an air hole 144, respectively. In one embodiment, the concentration detector 14 may be, but not limited to an integrated circuit (IC) chip.

In the above embodiments, a diameter of the plurality of holes is provided to allow an air flow passing through, and the air flow carries at least one particle of the particle millimeter 2.5 (PM 2.5); or to allow an air flow passing through, and the air flow containing at least one miniaturize particulate matter 146 to be detected. In one embodiment, the cross-sectional area having the larger area of the holes 16 is facing to the detect area 142, and this makes the air flow carrying the at least one miniaturize particulate matter 146 may pass through the cross-sectional area having the smaller area of the holes 16 (predetermined diameter of hole) and may be selected to enter the detect area 142 to disperse from the cross-sectional area having the larger area of the holes 16 to the detect area 142. Hence, the embodiments of the disclosure uses a semiconductor advanced process to make the TSV wafer serve as the filter 12 of the at least one miniaturize particulate matter 146, and acts with the designs of the diameter and the shape of the holes 16. This may reduce the blocking situations during selecting and filtering the at least one miniaturize particulate matter 146.

Figure 2A:
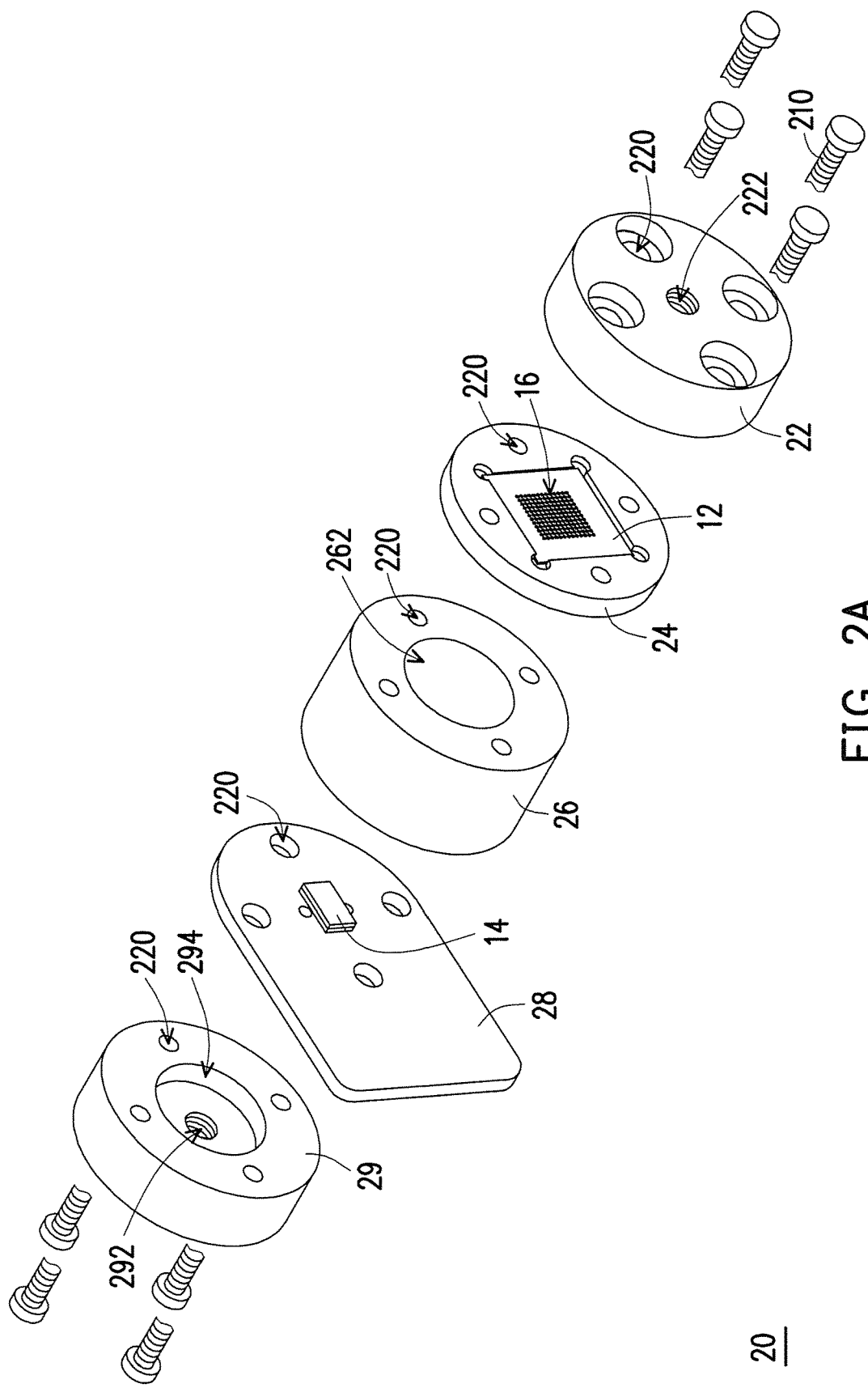
FIG. 2A is an exploded perspective schematic view of a miniaturize particulate matter detector according to an exemplary embodiment.

In an embodiment, the concentration detector 14 disposed on a printed circuit board (PCB) 28, as shown in FIG. 2A. And, each of two sides of the concentration detector 14 both sides is disposed an air hole 144 respectively, as shown in FIG. 1C.

In an embodiment, an oscillator 141 and a circuit 143 are included in the detect area 142. The oscillator 141 is electrically connected to the circuit 143. When the at least one miniaturize particulate matter 146 is attached to the oscillator 141, the oscillation frequency of the oscillator 141 is transferred into the mass change and the concentration of the at least one miniaturize particulate matter 146 is detected.

Figure 1D:
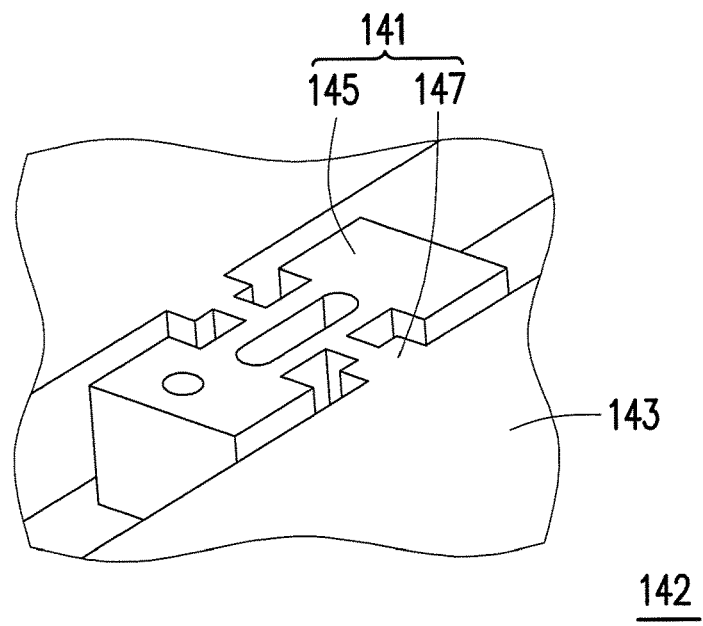
FIG. 1D is a schematic view of an oscillator according to an exemplary embodiment.

Please refer to FIG. 1D, the oscillator 141 further includes an oscillated element 145 and a spring 147 disposed at each of two sides of the oscillated element 145, respectively. The spring 147 is connected to the circuit 143. The circuit 143 is disposed on a circuit board 28, and the circuit 143 is electrically connected to the circuit board 28. In one embodiment, the circuit 143 located under the detect area 142. In an embodiment, the concentration detector 14 has at least one conductor 148 connected to the circuit board 28. The circuit 143 may be, but not limited to an IC chip. The oscillator 141 may be, but not limited to a Micro Electro-Mechanical System (MEMS) oscillator or a quartz oscillator.

Figure 1E:
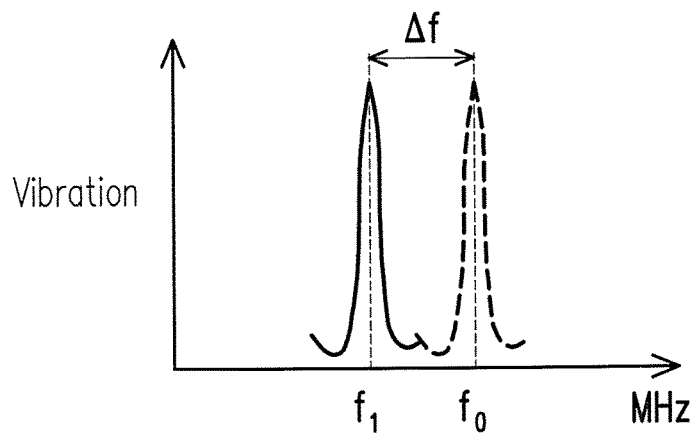
FIG. 1E and FIG. 1F are schematic views illustrating the working principle of an oscillator according to an exemplary embodiment.
Figure 1F:
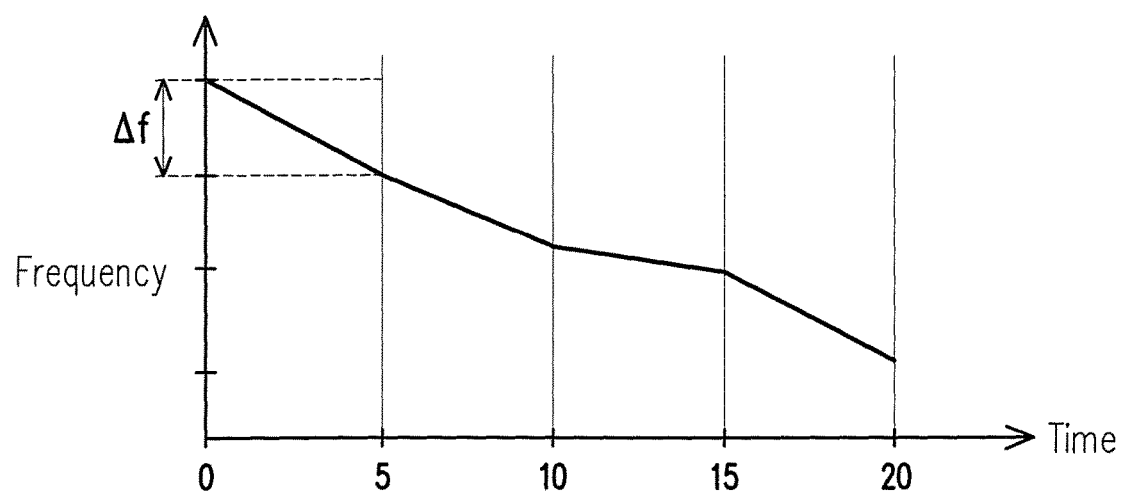

FIG. 1E and FIG. 1F are schematic views illustrating the working principle of an oscillator according to an exemplary embodiment. As shown in FIG. 1E, the vertical axis represents the number of oscillations, and the horizontal axis is represents the frequency. The formula is as follows:

$$f = \frac{1}{2\pi}\sqrt{\frac{k}{m}} \Rightarrow \frac{\Delta f}{f} = -\frac{\Delta m}{2m}$$

As shown in FIG. 1F, the vertical axis represents the frequency, and the horizontal axis represents the time. When the at least one miniaturize particulate matter 146 is attached to the oscillator 141, the oscillation frequency decreases, therefore, the oscillation frequency is transferred into the mass change and the concentration of the at least one miniaturize particulate matter 146 is detected.

FIG. 2A is an exploded perspective schematic view of a miniaturize particulate matter detector according to an exemplary embodiment. As shown in the embodiment of FIG. 2A, the miniaturize particulate matter detector 10 further includes an intermediate element 26, a top cover 22 and a bottom cover 29. The intermediate element 26 has a first through-holes 262 and the intermediate element 26 is disposed between the filter 12 and the concentration detector 14. The intermediate element 26 is disposed between a support plate 24 and the circuit board 28. The first through-hole 262 aligns with the plurality of holes 16 and the concentration detector 14 to make the air flow easily pass through the first through-hole 262. The intermediate element 26, the top cover 22 and the bottom cover 29 may have the same geometric shape. In one embodiment, the intermediate element 26, the top cover 22 and the bottom cover 29 may have a round shape to easily assembly a module or dismount the module.

The filter 12 is disposed between the top cover 22 and the intermediate element 26. The top cover 22 has an air inlet 222. The circuit board 28 is disposed between the bottom cover 29 and the intermediate element 26. The bottom cover 29 has an air outlet 292. In an embodiment, an inside surface of the top cover 22 has a first recess 224. An inside surface of the bottom cover 29 has a second recess 294. The first recess 224 and the second recess 294 communicated with the air inlet 222 and the outlet 292 respectively.

Figure 2B:
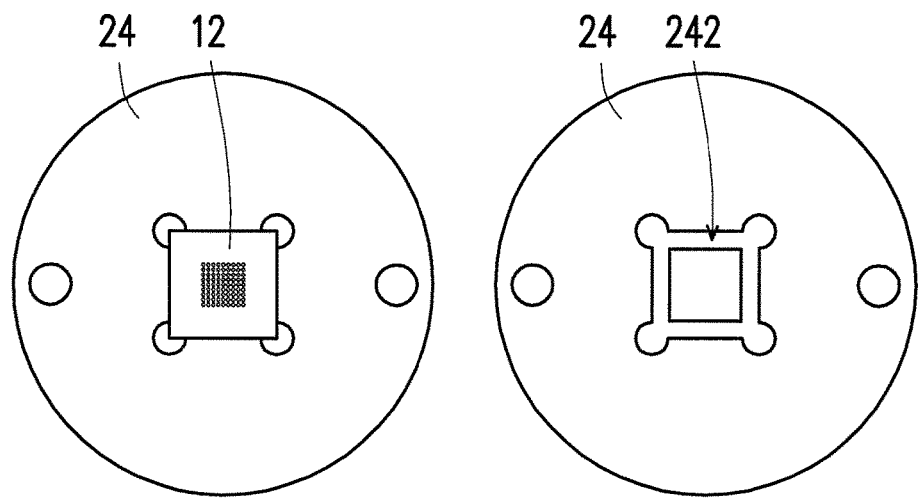
FIG. 2B is a perspective schematic view of a filter according to an exemplary embodiment.

FIG. 2B is an exploded perspective schematic view of a filter according to an exemplary embodiment. As shown in the embodiment of FIG. 2B, the filter 12 is disposed on the support plate 24 having a recess 242 thereon. The filter 12 is inserted and fixed inside the recess 242. The support plate 24 has a fifth through-hole, wherein the fifth through-hole and the filter 12 link together.

As shown in FIG. 2A and FIG. 2B, the top cover 22, the support plate 24, the intermediate element 26, the circuit board 28 and the bottom cover 29 dispose, respectively, a plurality of lock holes 220 thereon, to provide a plurality of keys 210 to lock the plurality of lock holes 220, and to fix the top cover 22, the support plate 24, the intermediate element 26, the circuit board 28 and the bottom cover 29 as one module 20.

Figure 3:
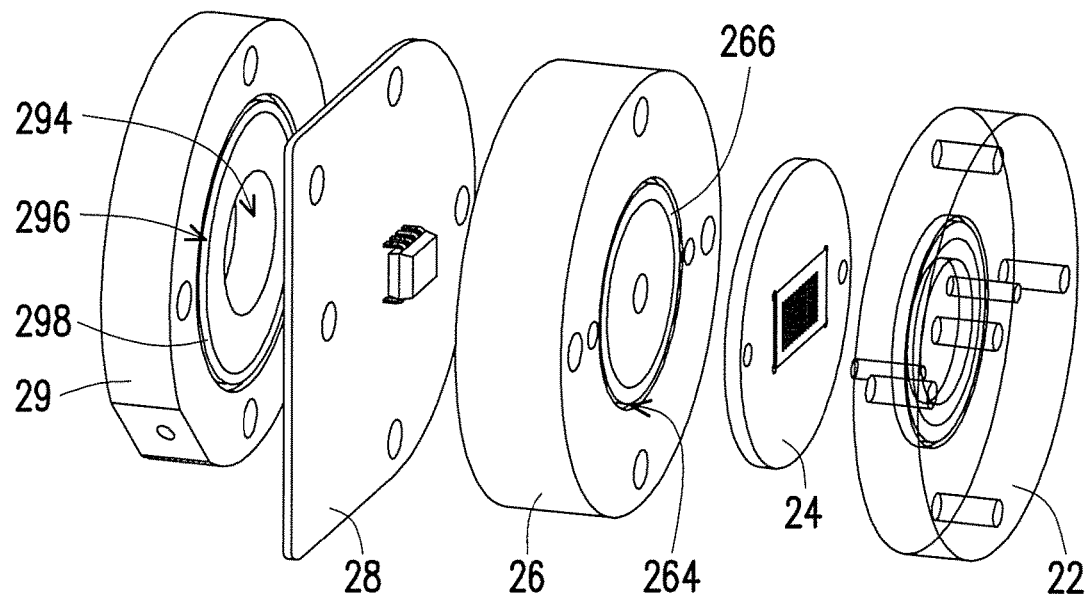
FIG. 3 is an exploded perspective schematic view of a miniaturize particulate matter detector according to a fourth exemplary embodiment.

FIG. 3 is an exploded perspective schematic view of a miniaturize particulate matter detector according to a fourth exemplary embodiment. As shown in the embodiment of FIG. 3, each of the two sides of the intermediate element 26 disposes a first groove 264 around the first through-hole 262 to provide a first seal element 266 embedded inside the first groove 264. A first Inside surface of the top cover 22 and a second inside surface of the bottom cover 29 dispose a second groove and a third groove (not shown in the drawings), respectively, to provide a second seal element (not shown in the drawings) and a third seal element 298, and the second seal element and the third seal element 298 are embedded in the second groove and the third groove 296 respectively. The first seal element 266 and the third seal element 298 provide a seal effect, therefore, the air flow passes through the filter 12 and the detector 14 without occurring any leakage. The embodiments of the disclosure may use a fixture design to change the filter 12 or the concentration detector 14 to repeatedly use the miniaturize particulate matter detector 10.

Figure 4:
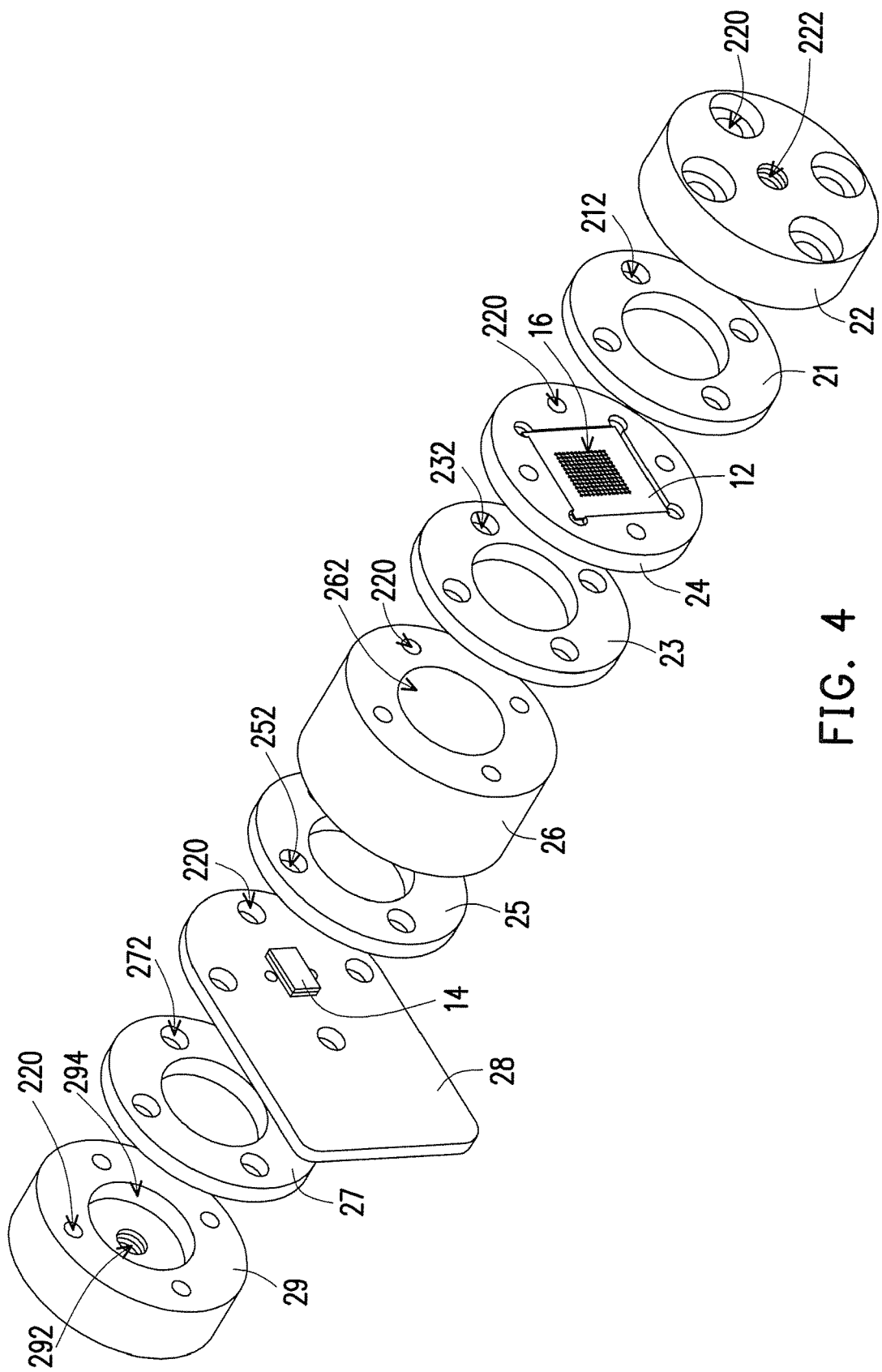
FIG. 4 is an exploded perspective schematic view of a miniaturize particulate matter detector according to a fifth exemplary embodiment.

FIG. 4 is an exploded perspective schematic view of a miniaturize particulate matter detector according to a fifth exemplary embodiment. As shown in the embodiment of FIG. 4, gaskets 21, 23, 25, and 27 are disposed between the top cover 22 and the support plate 24, between the support plate 24 and the intermediate element 26, between the intermediate element 26 and the circuit board 28, and between the circuit board 28 and the bottom cover 29, respectively, to provide a sealing effect and a buffering effect. The four gaskets 21, 23, 25, and 27 respectively disposes their own multiple locks 212, 232, 252, 272 thereon for corresponding to the top cover 22, the support plate 24, the intermediate element 26, the circuit board 28 and the lock holes 220 of the bottom cover 29, as shown in FIG. 4.

Figure 5A:
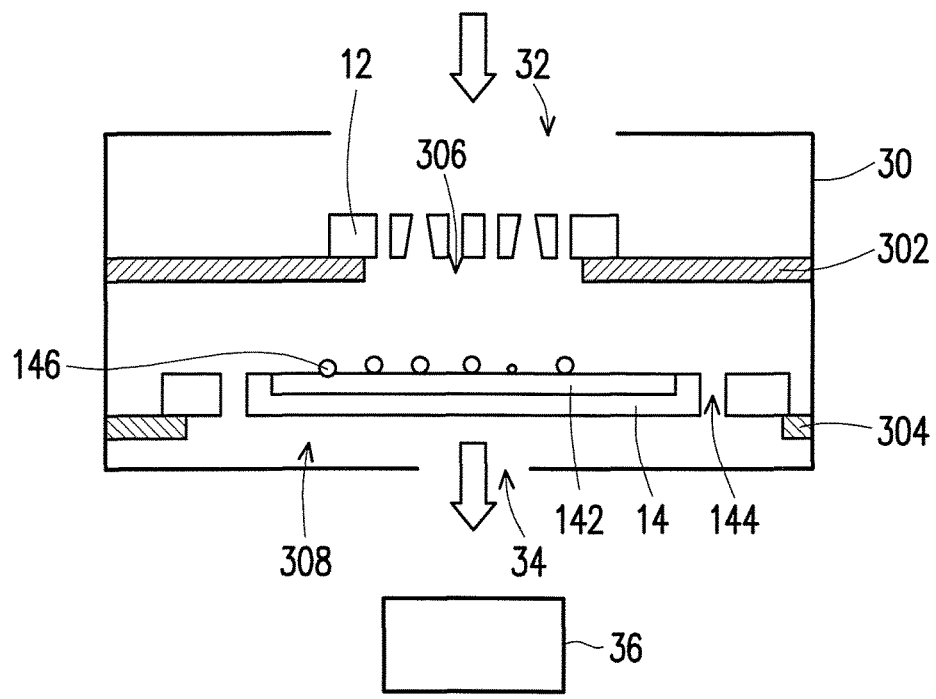
FIG. 5A is a cross-sectional schematic view of a miniaturize particulate matter detector according to a sixth exemplary embodiment.

FIG. 5A is a cross-sectional schematic view of a miniaturize particulate matter detector according to a sixth exemplary embodiment. As shown in the embodiment of FIG. 5A, a fixture 30 includes an inlet 32 and an outlet 34. A first support plate 302 and a second support plate 304 are disposed in the fixture 30. The first support plate 302 locates above the second support plate 304. The first support plate 302 has a third through-hole 306, and the filter 12 is disposed on the third through-hole 306. The second support plate 304 has a fourth through-hole 308, and the concentration detector 14 is disposed on the fourth through-hole 308. The concentration detector 14 has one or more air holes 144.

In an embodiment, a pump 36 is disposed at an outlet 34 of the fixture 30. The air flow may enter the filter 12 via an inlet 32 of the fixture 30, to filter the at least one miniaturize particulate matter 146. The at least one miniaturize particulate matter 146 that may pass through the filter 12 is attached to the detect area 142 of the concentration detector 14, therefore, the concentration of the at least one miniaturize particulate matter 146 is obtained.

In an embodiment, the interior of the fixture 30 may be cut into three spaces through the first support plate 302 and the second support plate 304. Thus, the air flow may be driven by the pump 36, and passes through the filter 12, the concentration detector 14, the air holes 144 from the inlet 32 of the fixture 30, then flows out form the outlet 34 of the fixture 30.

In an embodiment, after the filter 12 and the concentration detector 14 are modularized, the modularized filter 12 and the modularized concentration detector 14 may be disassembled and replaced.

Figure 5B:
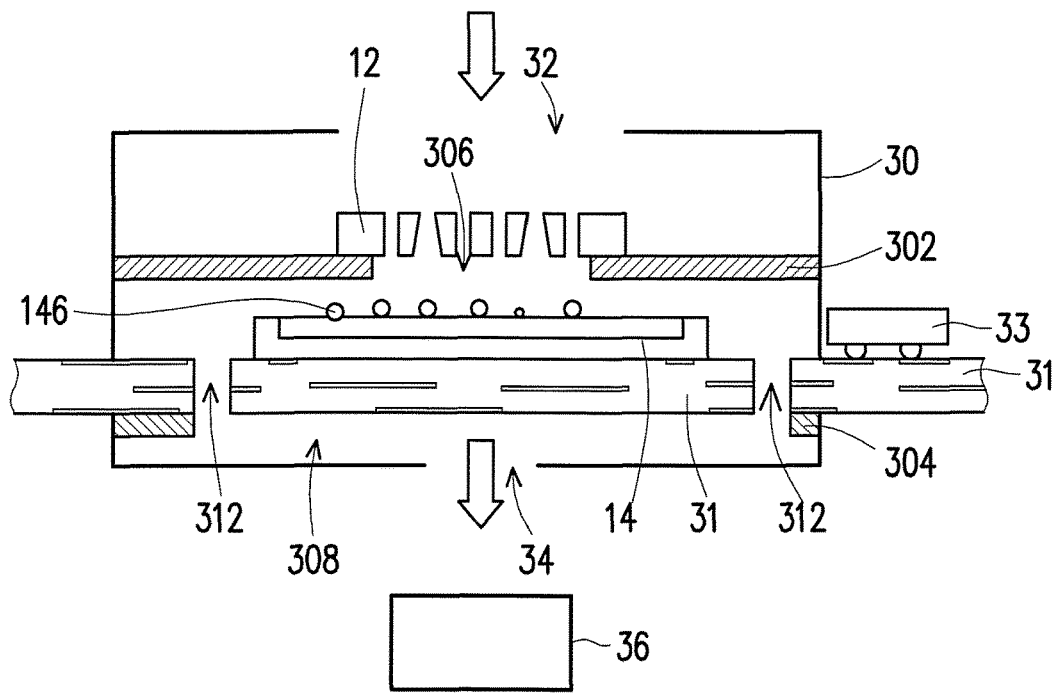
FIG. 5B is a cross-sectional schematic view of a miniaturize particulate matter detector according to a seventh exemplary embodiment.

FIG. 5B is a cross-sectional schematic view of a miniaturize particulate matter detector according to a seventh exemplary embodiment. Basically, the embodiment in FIG. 5B is similar to that in FIG. 5A. As shown in the embodiment of FIG. 5B, the difference is a printer circuit board 31 (PCB) is disposed on the second support plate 304, and the PCB 31 is protruding from the fixture 30 to connect another chip 33 or substrate and so on. The concentration detector 14 is electrically connected to and disposed on the PCB 31. In one embodiment, the concentration detector 14 has one or more air through holes (not shown in drawings). The pump 36 is disposed at the outlet 34 of the fixture 30 to drive the air flow. In one embodiment, the PCB 31 has a plurality of air through holes (not shown in drawings). Thus, the air flow may enter the filter 12 via the inlet 32 of the fixture 30, to filter the at least one miniaturize particulate matter 146. The at least one miniaturize particulate matter 146 that may pass through the filter 12 is attached to the detect area 142 of the concentration detector 14 the concentration of the at least one miniaturize particulate matter 146 is obtained. Then, the air flow may flow out form the outlet 34 of the fixture 30 via air through-holes 312.

Figure 5C:
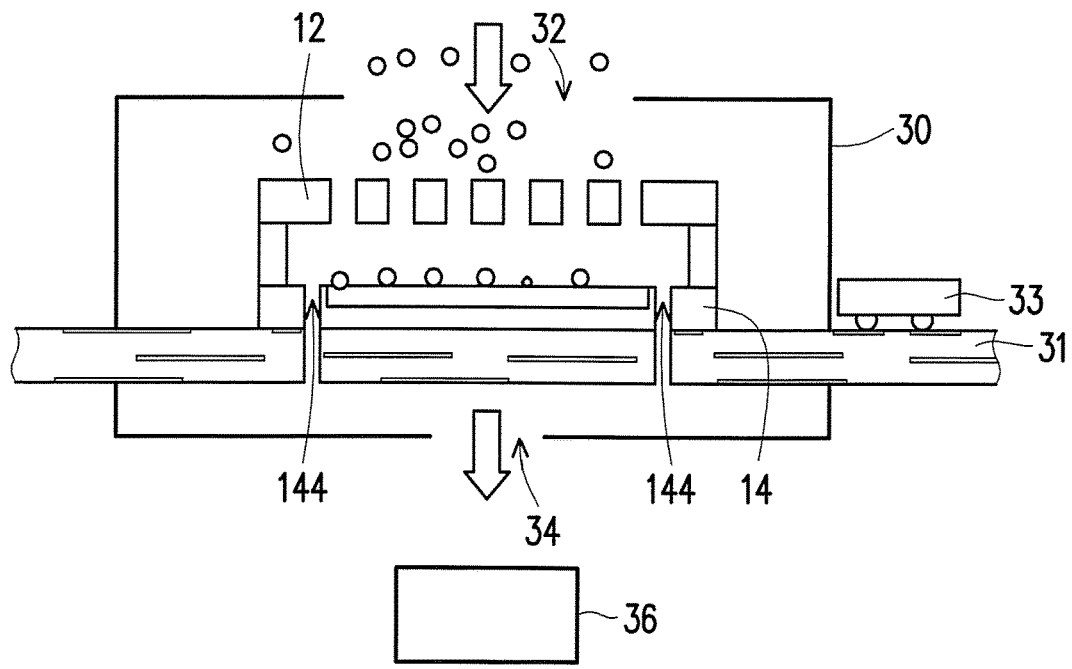
FIG. 5C is a cross-sectional schematic view of a miniaturize particulate matter detector according to an eighth exemplary embodiment.

FIG. 5C is a cross-sectional schematic view of a miniaturize particulate matter detector according to an eighth exemplary embodiment. In the embodiment of FIG. 5C, the embodiment shown in FIG. 1C is disposed on the PCB 31, and the air through-hole 144 of the concentration detector 14 passes through the PCB 31. Herein, the air flow may enter the filter 12 and the concentration detector 14 via the inlet 32 of the fixture 30, the air flow then passes through the air through-holes 144 and flows out from the outlet 34 of the fixture 30. The pump 36 is disposed at the outlet 34 of the fixture 30 to drive the air flow.

Figure 5D:
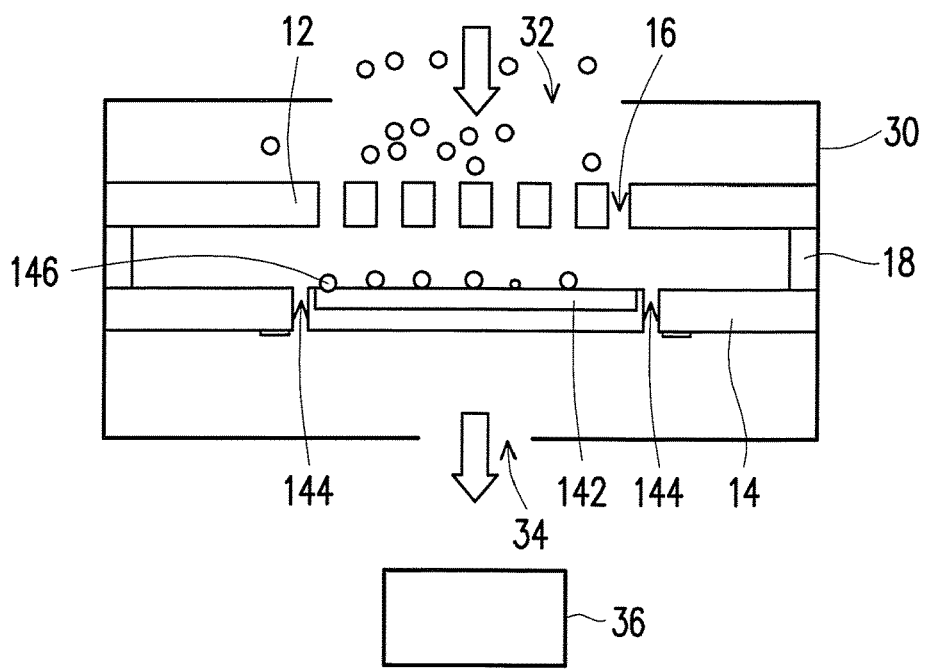
FIG. 5D is a cross-sectional schematic view of a miniaturize particulate matter detector according to a ninth exemplary embodiment.

FIG. 5D is a cross-sectional schematic view of a miniaturize particulate matter detector according to a ninth exemplary embodiment. In the embodiment of FIG. 5D, the embodiment shown in FIG. 1C is disposed on an inside surface of the fixture 30. The air flow may enter the filter 12, the concentration detector 14, and the air through holes 144 via the inlet 32 of the fixture 30, the air flow then flows out from the outlet 34 of the fixture 30. The pump 36 is disposed at the outlet 34 of the fixture 30 to drive the air flow. Same as shown in FIG. 1C, an adhesive material 18 is disposed between the filter 12 and the concentration detector 14 of FIG. 5D to bonding the filter 12 and the detector 14.

Figure 5E:
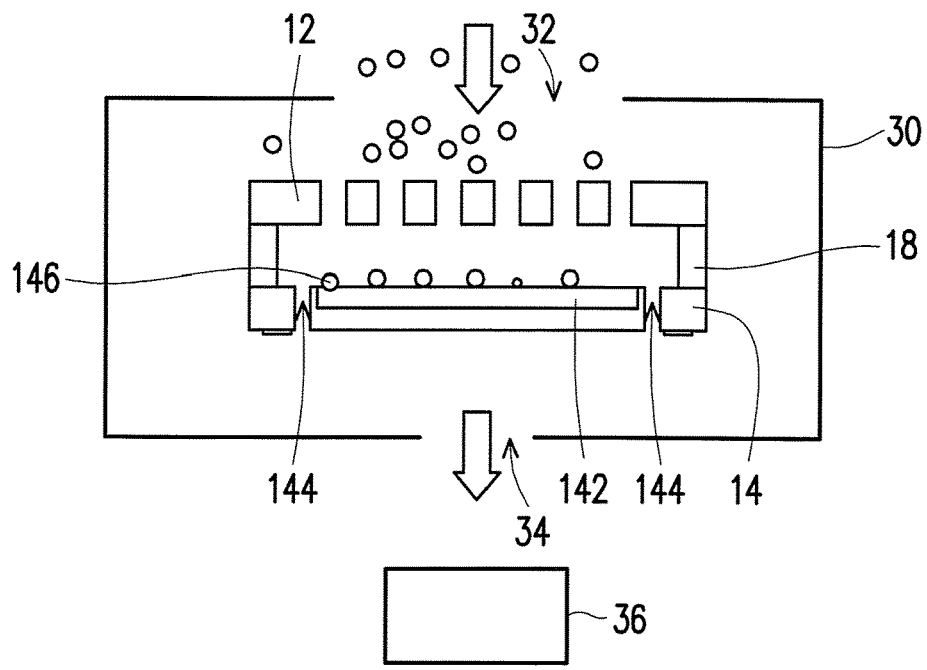
FIG. 5E is cross-sectional schematic view of a miniaturize particulate matter detector according to a tenth exemplary embodiment.

FIG. 5E is cross-sectional schematic view of a miniaturize particulate matter detector according to a tenth exemplary embodiment. In the embodiment of FIG. 5E, the embodiment shown in FIG. 1C is disposed on the interior of the fixture 30. The air flow may enter the filter 12, the interior of the fixture 30, and the concentration detector 14 via the inlet 32 of the fixture 30, the air flow then flows out from the outlet 34 of the fixture 30. In one embodiment, the concentration detector 14 does not dispose the air through-hole. In one embodiment, the pump 36 is disposed at the outlet 34 of the fixture 30 to drive the air flow.

Figure 6:
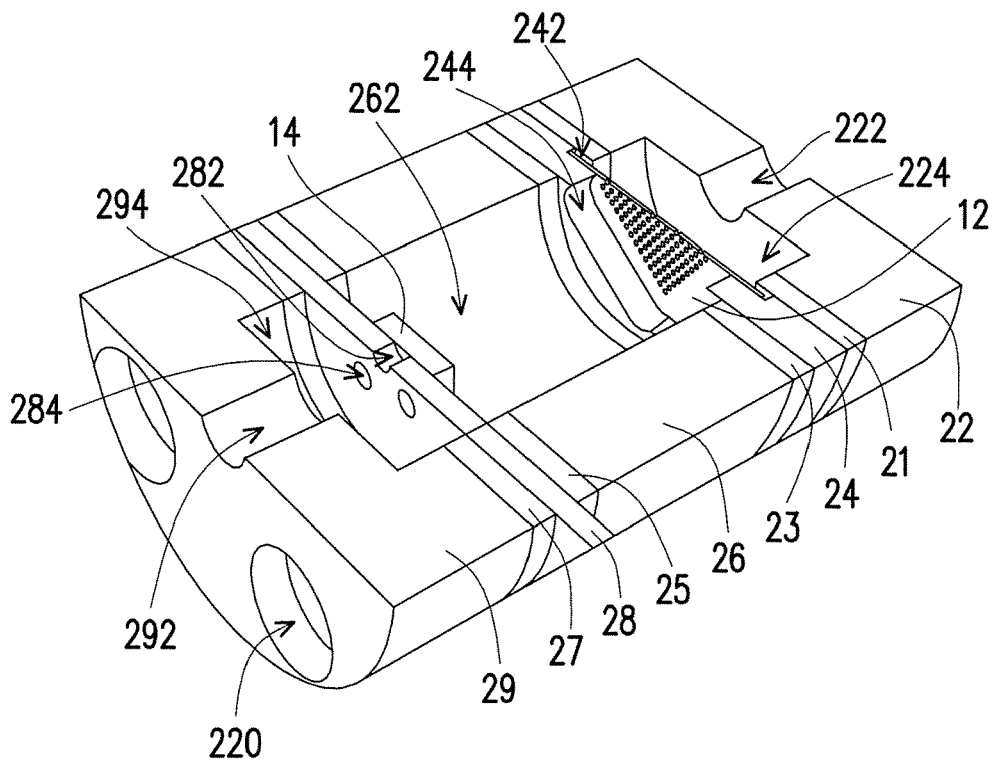
FIG. 6 is an assembled cross-sectional schematic view of a miniaturize particulate matter detector according to a tenth exemplary embodiment.

FIG. 6 is an assembled cross-sectional schematic view of a miniaturize particulate matter detector according to a tenth exemplary embodiment. Please refer to FIG. 6, after modularization, a gasket 21 is disposed between the top cover 22 and the support plate 24. The top cover 22 has an air inlet 222, and there is a first recess 224 inside the top cover 22 to communicate with the air inlet 222. The filter 12 is disposed on the support plate 24 to correspond to the fifth through-hole 244 of the support plate 24, then the air flow passes through the filter 12 and the fifth through-hole 244. The gasket 25 is disposed between the intermediate element 26 and the circuit board 28. The concentration detector 14 is disposed on the circuit board 28, and the circuit board 28 disposes a second through-hole 282 corresponding to the oscillator 141 of the concentration detector 14. The second through-hole 282 is disposed on the circuit board 28 to correspond to the concentration detector 14, and this may make the air flow pass through the oscillator 141 of the concentration detector 14, then enter the second through-hole 282. On circuit board 28, at least one a first air through-hole 284 may be disposed at both sides of the concentration detector 14. The first through-hole 262 of the intermediate element 26 may communicate with the fifth through-hole 244 of the support plate 24, the first air through-hole 284 and the second air through-hole 282, respectively. There is a second recess 294 in the inside of the bottom cover 29, which communicates with the air outlet 292, the first air through hole 284 and the second through hole 282, respectively. A gasket 27 is disposed between the bottom cover 29 and the circuit board 28. A gasket 25 is disposed between the intermediate element 26 and the circuit board 28. The top cover 22, the support plate 24, the intermediate element 26, the circuit board 28 and the bottom cover 29 may use a plurality of keys to lock the plurality of lock holes. After these components in the aforementioned embodiments of the disclosure are modularized, the modularized products of the disclosure may be miniaturized, easy to carry, real-time proceeding to detect the at least one miniaturize particulate matter 146.

Figure 7:
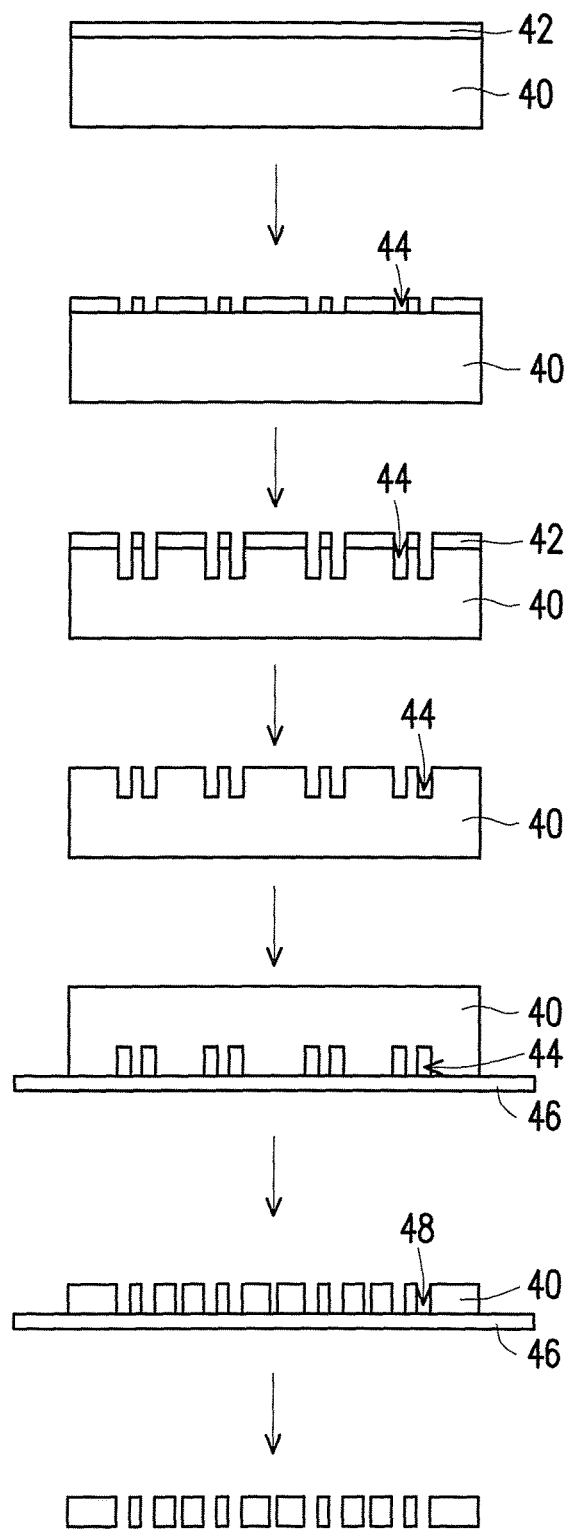
FIG. 7 is a schematic view of a manufacturing method of a filter according to an exemplary embodiment.

FIG. 7 is a schematic view of a manufacturing method of a filter according to an exemplary embodiment. Please refer to FIG. 7, the manufacture method of the filter may comprise: providing a substrate 40; coating or lithographic printing a photoresist material 42 on the substrate 40; etching a plurality of openings 44 on the substrate 40, wherein the plurality of openings 44 have an opening shape of gradually reducing, or gradually expanding or cylindrical; removing the photoresist material 42 from the substrate 40; pasting a first support plate 46 on a surface of the plurality of openings 44 of the substrate 40; grinding the substrate 40 until to expose the plurality of openings 44 to form a plurality of through-silicon vias (TSVs) 48; and cutting the substrate 40 and includes a plurality of TSV 48.

Figure 8A:
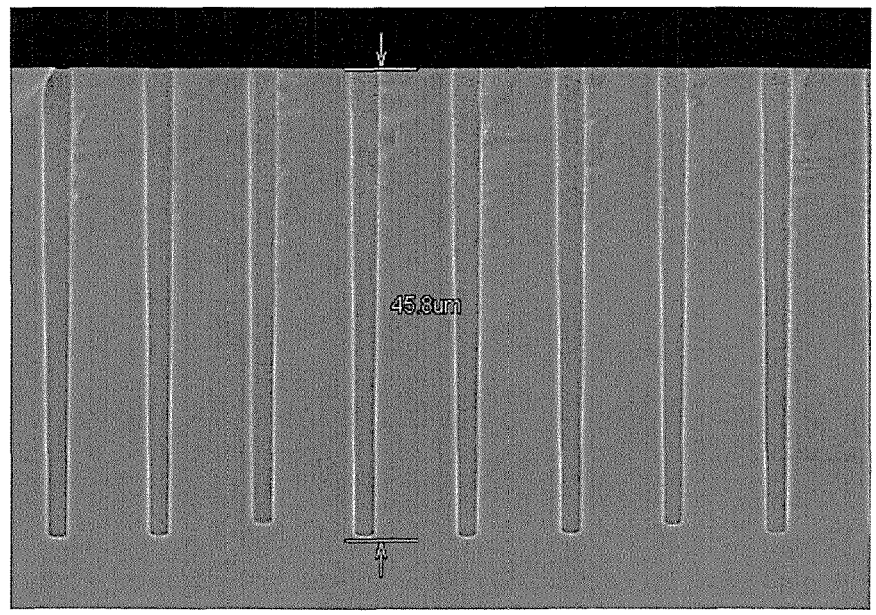
FIG. 8A, FIG. 8B, and FIG. 8C are schematic views of TSV images of a filter according to an exemplary embodiment.
Figure 8B:
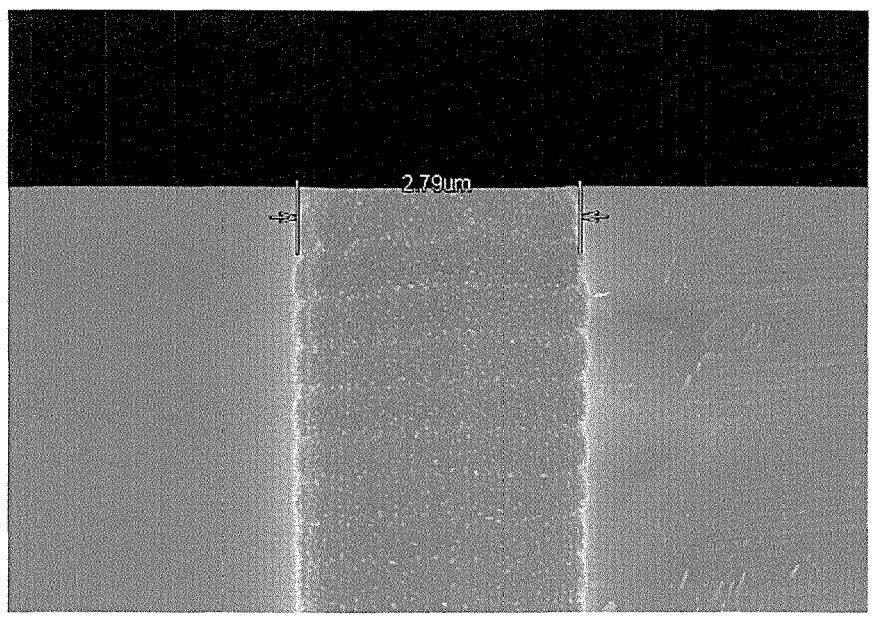
Figure 8C:
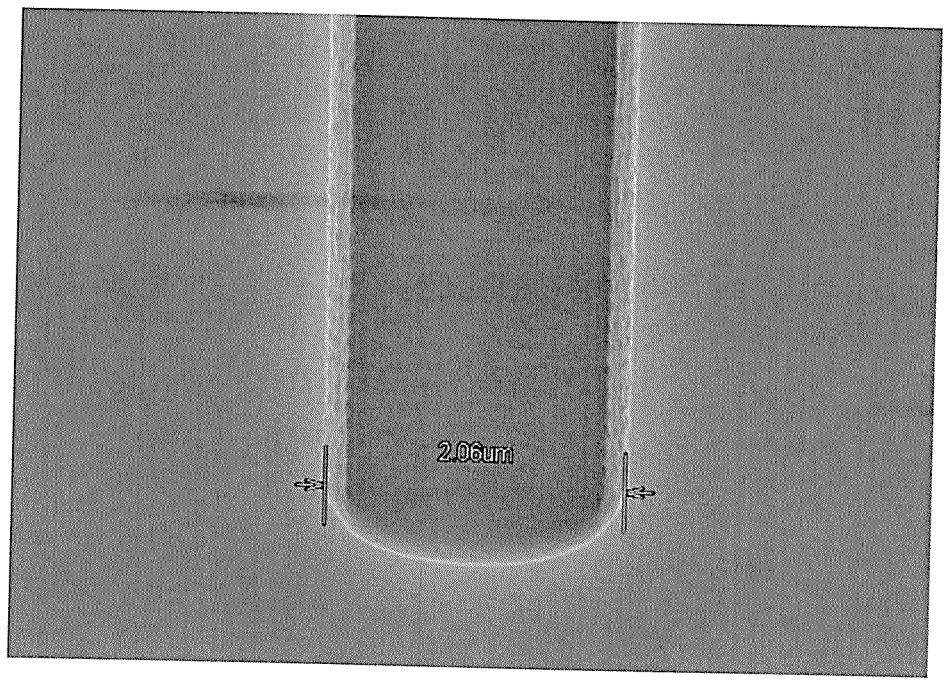

FIG. 8A, FIG. 8B, and FIG. 8C are schematic views of TSV images of a filter according to an exemplary embodiment. Please refer to FIG. 8A, FIG. 8B, and FIG. 8C, the opening size may be obtained by using the developer and an etching scheme, and using the etching scheme may etch specific angles for the holes, as shown in FIG. 8A. In FIG. 8A, the TVS is made by using etching, and the etching depth is 45 um. It may be seen from FIG. 8B and FIG. 8C, the central diameter (CD) of the top is 2.79 um and the CD of the bottom is 2.06 um. The filter may be obtained by grinding, polishing and cutting the wafer.

According to the exemplary embodiments provided herein, the disclosure at least includes the characteristics of the exemplary embodiments of using the developer and the etching scheme to make the TSV filter, and this may greatly reduce the selecting number of the opening size and the inlet sizes for detecting the miniaturize particulate matter; arrangement of modularized detector, for example, MEMS oscillator or quartz oscillator, and this may miniaturize these modules; having a replaceable function to replace the filter that has no more filtering function or to replace the detector that is supersaturated; batching and carrying on huge production assembly, and this may reduce the costs; modularizing products, and this may lead portable products, for example, cellphone.

Therefore, the disclosed exemplary embodiments of the disclosure may develop and achieve miniaturized modules for detecting miniaturize particulate matters. Also, the disclosed exemplary embodiments may widely be applied to portable products, widely monitoring, and so on. This may stay away from pollution of miniaturize particulate matters, find out the sources of causing the pollution, and reduce the chances that may cause lung cancer.

It will be apparent to those skilled in the art that various modifications and variations can be made to the disclosed embodiments of the disclosure. It is intended that the specification and examples be considered as exemplary embodiments only, with a scope of the disclosure being indicated by the following claims and their equivalents.

What is claimed is:

1. A miniaturized particulate matter detector, comprising:
a filter having a plurality of holes; and
a concentration detector correspondingly disposed under the filter, wherein the concentration detector has a detect area used for detecting a concentration of at least one miniaturized particulate matter,
wherein all or part of the plurality of holes have an opening shape of gradually reducing or a gradually expanding, and the plurality of holes are through-silicon vias.

2. The miniaturized particulate matter detector of claim 1, wherein a diameter of the plurality of holes is provided to allow an air flow passing through, and the air flow carries at least one particle with a diameter of 2.5 micrometers or less.

3. The miniaturized particulate matter detector of claim 1, wherein the concentration detector is disposed on a circuit board, and both sides of the concentration detector are respectively disposed in an air through-hole.

4. The miniaturized particulate matter detector of claim 1, wherein an oscillator and a circuit are included in the detect area, the oscillator is electrically connected to the circuit, and when the at least one miniaturized particulate matter is attached to the oscillator, an oscillation frequency of the oscillator decreases and the concentration of the at least one miniaturized particulate matter is detected.

5. The miniaturized particulate matter detector of claim 4, wherein the circuit is disposed on and electrically connected to a circuit board, and the detector further includes the circuit board and at least one conductor electrically connected to the circuit board,
wherein the circuit board disposes a second through-hole corresponding to the concentration detector, and an air flow passes through the oscillator of the concentration detector and enters the second through hole.

6. The miniaturized particulate matter detector of claim 1, further including:

an intermediate element having two sides and a first through-hole, the intermediate element is disposed between the filter and the concentration detector, and the first through-hole is aligned with the plurality of holes and the concentration detector;

a top cover having an air inlet, wherein the top cover and the filter are disposed correspondingly to one side of the intermediate element; and a bottom cover having an air outlet, wherein the bottom cover and the concentration detector are disposed correspondingly to the other side of the intermediate element.

7. The miniaturized particulate matter detector of claim 6, wherein the filter is disposed on a support plate having a recess thereon, and the filter is inserted inside the recess.

8. The miniaturized particulate matter detector of claim 7, wherein the concentration detector is disposed on a circuit board; and the top cover, the support plate, the intermediate element, the circuit board and the bottom cover dispose, respectively, a plurality of lock holes thereon to provide a plurality of keys to fix the top cover, the support plate, the intermediate element, the circuit board and the bottom cover to form a module.

9. The miniaturized particulate matter detector of claim 6, wherein each of the two sides of the intermediate element disposes a first groove, and a first seal element is embedded inside the first groove; and a first inside surface of the top cover and a second inside surface of the bottom cover dispose a second groove and a third groove, respectively, and a second seal element and a third seal element are embedded in the second groove and the third groove, respectively.

10. The miniaturized particulate matter detector of claim 6, wherein the concentration detector is disposed on a circuit board; four gaskets are disposed between the top cover and the support plate, between the support plate and the intermediate element, between the intermediate element and the circuit board, and between the circuit board and the bottom cover, respectively, to provide a buffering effect; and each of the four gaskets disposes a plurality of lock holes to provide a plurality of keys to fix the top cover, the support plate, the intermediate element, the circuit board and the bottom cover.

* * * * *